United States Patent [19]

King, III et al.

[11] Patent Number: 4,927,898

[45] Date of Patent: May 22, 1990

[54] POLYSILOXANES WITH STERICALLY HINDERED HETEROCYCLIC MOIETY

[75] Inventors: Roswell King, III, Pleasantville, N.Y.; George N. Foster, Bloomsbury, N.J.; Herbert E. Petty, Bethel, Conn.

[73] Assignee: Union Carbide Chemicals and Plastics Company Inc., Danbury, Conn.

[21] Appl. No.: 240,505

[22] Filed: Sep. 6, 1988

[51] Int. Cl.$^5$ .............................................. C08G 77/04
[52] U.S. Cl. ........................................ 528/27; 528/28; 544/229; 546/14; 548/110; 548/406
[58] Field of Search ...................... 546/14; 528/27, 28; 548/110, 406; 544/229

[56] References Cited

U.S. PATENT DOCUMENTS

| | | | |
|---|---|---|---|
| 3,975,357 | 8/1976 | Murayama et al. | 260/45.8 N |
| 4,123,418 | 10/1978 | Gilg et al. | 260/45.8 N |
| 4,177,186 | 12/1979 | Rody et al. | 260/45.8 N |
| 4,232,131 | 11/1980 | Rody et al. | 525/184 |
| 4,233,410 | 11/1980 | Rody et al. | 525/123 |
| 4,233,412 | 11/1980 | Rody et al. | 525/167 |
| 4,234,699 | 11/1980 | Rody et al. | 525/55 |
| 4,260,689 | 4/1981 | Rody et al. | 525/55 |
| 4,260,691 | 4/1981 | Rody et al. | 525/130 |
| 4,684,726 | 8/1987 | Greco et al. | 544/69 |

FOREIGN PATENT DOCUMENTS 1399239 6/1975 United Kingdom .

OTHER PUBLICATIONS

Cordonnier, "LLDPE and U Vaging", Plast. & Rub. Proc. & Applic., 8, (1987), 23–27.
Stengrevics et al., "Stabilization of Filled Polyolefins", Plast. Compounding, Jul./Aug. 1987, 35.
Andrianov et al., "Polyiminooxy- and Polyaminooxyorganosiloxanes", Dokl. Akad. Nauk. SSSR, 206, No. 3, 616–619, Sep. 1972.

*Primary Examiner*—Melvyn I. Marquis
*Attorney, Agent, or Firm*—Bonnie L. Deppenbrock

[57] ABSTRACT

A polysiloxane having pendant, sterically-hindered heterocyclic moieties attached to a siloxane chain, and their use in stabilizing synthetic polymer compositions.

31 Claims, No Drawings

POLYSILOXANES WITH STERICALLY HINDERED HETEROCYCLIC MOIETY

FIELD OF THE INVENTION

The present invention is directed to polysiloxanes having pendant sterically hindered heterocyclic moieties attached to the siloxane chain; such as the sterically hindered piperidinoxy polysiloxanes. These compounds can be represented by the general formula $M_{y'}^{*}D_{x}D_{y}^{*}T_{z}Q_{w}M_{y'}^{*}$ and can be used to stabilize synthetic polymer compositions.

BACKGROUND

One of the frequent problems encountered with synthetic polymers is instability on exposure to light, heat and atmospheric conditions, leading to deterioration and color change. Over the years industry has developed many additives that are blended into the polymer to alleviate the problem and is still continuously searching for new materials that will prolong the life of the polymeric product. In addition to the above harmful conditions, many polymers contain metal catalyst residues that can exert adverse effects on the synthetic polymer fiber, film, or other article.

The use of additives, collectively called stabilizers, to prevent or inhibit degradation of natural and synthetic materials is known. It is also known that a compound that stabilizes against heat and/or oxygen degradation in a material may not stabilize against light degradation in the same material, and vice versa. It is further known that a compound which exerts some form of stabilization in one type of synthetic or natural material may be completely ineffective in another type of material. Thus, compounds are classified as antioxidants, light stabilizers, heat stabilizers, etc., depending upon the stabilizing effect a particular compound may have on a specific material or type of material. As a consequence, in many cases mixtures of stabilizers are used to obtain desired protection against one or more forms of degradation.

It has now been found that a novel class of polysiloxanes having sterically hindered heterocyclic moieties can be produced that stabilize synthetic polymers against the deleterious effect caused by exposure to light, in particular to ultraviolet light radiation in sunlight.

The use of the heterocyclic piperidine compounds as stabilizers in synthetic polymers has been disclosed. Thus, in U.S. Pat. No. 3,975,357, issued to Murayama et al. on Aug. 17, 1976, a large number of 1-substituted-2,2,6,6-tetramethylpiperidines were disclosed as synthetic polymer stabilizers. However, there is no mention of siloxanes.

In U.S. Pat. No. 4,123,418, issued to Gilg et al. on Oct. 31, 1978, sterically hindered cyclic amines are used to stabilize styrene polymers, such as ABS resins; the patent contains no mention of siloxanes.

The stabilizers disclosed in U.S. Pat. No. 4,177,186, issued to Rody et al. on Dec. 4, 1979, are the 4-siloxy derivatives of alkylated piperidines. Though a large number of siloxys are disclosed none of them are within the scope of this instant invention, nor do they suggest the polysiloxanes of this invention.

In a series of patents issued to Rody et al. in late 1980 and early 1981 (U.S. Pat. Nos. 4,232,131; 4,233,410; 4,233,412; 4,234,699; 4,260,689; 4,260,691; all divisions or continuation-in part of Ser. No. 896,676) there is a common disclosure of sterically hindered polyalkypiperidine compounds including polysilylesters and their use as stabilizers. None of these patents, however, suggest or disclose the polysiloxanes having sterically hindered heterocyclic moieties as defined by the general or specie formulas set forth in this instant specification.

In U.S. Pat. No. 4,684,726, issued to Greco et al. on Aug. 4, 1987, there is disclosed the reaction of silanes with compounds containing a sterically hindered amine group. However, there is no suggestion or disclosure on the use of polysiloxanes as reactants to produce the polysiloxanes of this invention containing the sterically hindered heterocyclic moiety.

United Kingdom Patent Specification No. 1,399,239, issued to Ciba-Geigy AG, published June 25, 1975, relates to novel piperidine derivative, however, none of the compounds are siloxane products.

The use of hindered amine light stabilizers (HALS) is discussed in the article "LLDPE and UV aging" by M. Cordonnier, Plast. & Rub. Proc. & Applic. 8 (1987) 23–27. Though reference to 3 HALS materials is made in Table 7 only one is specifically identified, Tinuvin 622, which is not a polysiloxane; there is no mention or suggestion of polysiloxanes.

In "Stabilization of filled polyolefins" E. Stengrevics et al., Plast. Compounding July/August 1987, 35, the use of oligomeric hindered piperidine derivatives as stabilizers is disclosed. However, none of these HALS compounds are polysiloxanes.

Processes for the production of "Polyiminooxy- and Polyaminoalkoxyorganosiloxanes" are shown by K. A. Andrianov et al., Dokl. Akad. Nauk SSSR, 20, No. 3, 616-619, Sept., 1972. This article shows the production of polysiloxanes, however, the compounds shown are not those of this instant invention.

In "The Antioxidizing Effect of Sterically Hindered Amines in Thermal Oxidation of Low Density Polyethylene", v. Dobrescu et al., Eur. Polym. J., 24, No. 3, 289–294 (1988) the stabilizing effect of the sterically hindered amine light stabilizers (HALS) shown in Table 1 on polyolefins was studied. None of the HALS compounds are polysiloxanes, nor are any siloxane compounds per se disclosed or suggested.

SUMMARY OF THE INVENTION

The present invention is directed to novel polysiloxanes of formula (I) below, which contain a sterically hindered heterocyclic moiety, of the general formula:

$$M_{y'}^{*}D_{x}D_{y}^{*}T_{z}Q_{w}M_{y'}^{*} \tag{I}$$

DESCRIPTION OF THE INVENTION

Though some sterically hindered amine compounds have been disclosed in the prior art, to the best of our present knowledge the prior art has not disclosed compounds defined by Formula (I), nor have such compounds been suggested.

The polysiloxanes of this invention containing the sterically hindered heterocyclic moiety have recurring groups of both the D unit and the D* unit in the polysiloxane chain, these units being represented by the formulas shown below, in which the sterically hindered heterocyclic moiety is attached to the silicon atom of the D* unit of the siloxane chain by a connecting link.

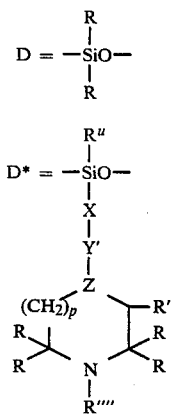

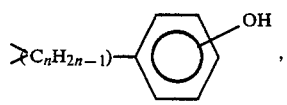

wherein R is phenyl or a lower alkyl group having from 1 to 3 carbon atoms, preferably methyl; R' is hydrogen or a lower alkyl group having 1 to 3 carbon atoms, or a keto oxygen (=O), preferably hydrogen; and X is nothing or a divalent linking group such as $-C_nH_{2n}-$, $-C_nH_{2n}-O-C_mH_{2m}-$,

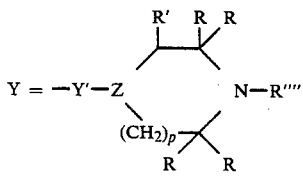

or

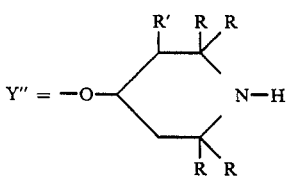

wherein n has a value of from 0 to about 10, preferably 3 and m has a value of from 0 to about 10; Y' is —O— or —COO— or $-C_nH_{2n}O-$; Z is a carbon or nitrogen atom, with the proviso that when Z is nitrogen Y' is $-C_nH_{2n}O-$; p has a value of zero or one; $R^u$ is an alkyl group having from 1 to about 8 carbon atoms, preferably from 1 to 3 carbon atoms, phenyl or phenethyl; and R'''' is hydrogen or alkyl having from 1 to about 12 carbon atoms.

For the sake of simplicity the heterocyclic moiety is hereby designated by the symbol Y, and Y represents the group:

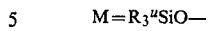

The piperidinoxy group is herein designated by the symbol Y''', and Y''' represents the group:

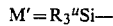

The polysiloxane chain also contains terminal units that can be either M, M' or M'' units, these units being represented by the formulas:

$M = R_3''SiO-$ $M' = R_3''Si-$ $M'' = R''O_{\frac{1}{2}}-$ wherein R'' is an alkyl group having from 2 to about carbon atoms, preferably from about 12 to about carbon atoms; or a phenyl group, unsubstituted or substituted, linear or branched.

As is known the substituents on a single silicon atom need not all be the same. Thus, they can all be methyl groups or they can be a combination of two or more alkyl groups or other of the groups heretofore defined.

The polysiloxane chain can also contain any of the other siloxane units known to those skilled in the art.

Included among the polysiloxanes of this invention are the branched or star type polymers that contain either the T unit or the Q unit, or both, in the polysiloxane chain, these units being represented by the formulas:

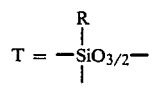

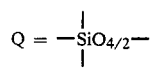

The polysiloxanes of this invention containing the sterically hindered heterocyclic moiety can be represented by the general formula:

$$M_v^* D_x D_y^* T_z Q_w M_v^* \qquad (I)$$

wherein
M* represents the M, M' and M'', units;
v has a value of 1;
x has a value of from 0 to about 200, preferably from 1 to about 20;
y has a value of from 1 to about 100, preferably from 1 to about 20;
z has a value of from zero to about 5, preferably zero;
w has a value of from zero to about 5, preferably zero; and
D, D*, T and Q are as heretofore defined.

Subgenerically the polysiloxanes (I) can be represented by the formulas:

$MD_x D_y^* T_z Q_w M'$  (IIA)

$M''D_x D_y^* T_z Q_w M''$  (IIB)

The preferred polysiloxanes (I) are those represented by the formulas:

$MD_x D_y^* M'$  (IIIA)

$M''D_x D_y M''$  (IIIB)

and the most preferred are those in which all of the R groups in the M, M', D, D* and M'' moieties are methyl groups.

Illustrative typical polysiloxane polymers of this invention are listed in Table I. In this table the numerals below the siloxane units identified in the heading indicate the average number of each such unit in the polymer chain, keeping in mind, as is known in the art, that all of a specifically identified unit need not necessarily be confined to a single segment in the polymer molecule.

TABLE I

| M | M" | D | D* | T | Q | M" | M' |
|---|---|---|---|---|---|---|---|
| 1 | 0 | 0 | 1 | 0 | 0 | 0 | 1 |
| 0 | 0 | 0 | 4 | 0 | 0 | 0 | 0 |
| 1 | 0 | 15 | 5 | 0 | 0 | 0 | 1 |
| 1 | 0 | 10 | 5 | 0 | 0 | 0 | 1 |
| 1 | 0 | 5 | 5 | 0 | 0 | 0 | 1 |
| 0 | 1 | 0 | 4 | 0 | 0 | 1 | 0 |
| 0 | 1 | 4 | 4 | 0 | 0 | 1 | 0 |
| 1 | 0 | 5 | 9 | 0 | 0 | 0 | 1 |
| 1 | 0 | 0 | 10 | 0 | 0 | 0 | 1 |
| 1 | 0 | 10 | 10 | 0 | 0 | 0 | 1 |
| 1 | 0 | 5 | 10 | 0 | 0 | 0 | 1 |
| 1 | 0 | 5 | 15 | 0 | 0 | 0 | 1 |
| 1 | 0 | 15 | 15 | 1 | 0 | 0 | 2 |
| 1 | 0 | 20 | 20 | 0 | 1 | 0 | 3 |

Illustratively, the polysiloxanes are conveniently produced by the catalytic reaction of a hindered piperidinol with a siloxane having a reactive hydrogen atom attached to a silicon atom via a dehydrocondensation reaction; the siloxane has ≡Si—H groups in the molecule. This reaction is known and it is also known that the transition metals are suitable catalysts and that they are generally used in the form of transition metal compounds such as cycloacta-1,5-diene diiodoplatinum (II), $H_2PtCl_6 \cdot 6H_2O$, bis-triphenylphosphine platinum diiodide, bis-triphenylphosphine carbonyl iridium (I) chloride, bis-triphenylphosphine carbonyl rhodium (I) chloride, palladium acetylacetonate, and the like. Any catalytic amount sufficient to catalyze the dehydrocondensation reaction can be used, e.g., from about 50 ppm or less to about 1,000 ppm or more transition metal atom, preferably from about 100 ppm to about 500 ppm, most preferably from about 150 ppm to about 300 ppm, based on the amount of polysiloxane starting material.

In addition any of the other known processes for reacting a hydrosilane with a functional hydroxyl group or oxirane group can be used. Such processes are discussed in the literature, for example, B. Boyer et al., J. Organomet. Chem., 148 (1978) C1–C4 and J. Organomet Chem., 157 (1978) 153–162; Blackburn et al., J. Organomet. Chem., 192 (1980) 329–338.

In the reaction an inert solvent is used, such as xylene, mesitylene, or higher alkane. The solvent preferably has a boiling point above 125° C., and most preferably above about 135° C. The solvent is subsequently removed by distillation or desolvation techniques. The reaction is generally carried out at reflux temperature in the presence of the catalyst.

An alternative process involves the anionic base catalyzed dehydrocondensation of the piperidinol with the ≡Si—H containing siloxane as shown in Example 14.

The hindered heterocyclic amines used as starting materials for the production of the compounds of Formula (I) are represented by the general formula:

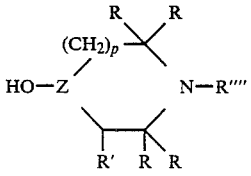

wherein R, R', R"" and Z are as previously defined. Illustrative thereof one can mention 2,2,6,6-tetra- methyl-4-piperidinol, 2,2,3,6,6-penta-methyl-4- piperidinol, 1,2,2,6,6-pentamethyl-4-piperidinol, N—(2-methylpropane-1-ol)-3,3,5,5-tetramethyl-2-piperazi none, 2,2,3,5,5-pentamethyl-4-methylolpyrrolidine and the like.

The ≡Si—H containing siloxane starting materials that are reacted with the hindered amines (IV) to produce the polysiloxanes (I) of this invention can be represented by the general formula:

$$M^*D_xD_y'T_zQ_wM^* \qquad (V)$$

Subgenerically the ≡Si—H containing siloxanes (V) can be represented by the formulas:

$$MD_xD_y'T_zQ_wM' \qquad (VIA)$$

$$M''D_xD_y'T_zQ_wM'' \qquad (VIB)$$

The preferred ≡Si—H containing siloxanes (V) are those represented by the formulas:

$$MD_xD_y'M' \qquad (VIIA)$$

$$M''D_xD_y'M'' \qquad (VIIB)$$

and the most preferred are those in which all of the R groups in the M, D, D' and M' moieties are methyl groups.

In Formulas V, VIA, VIB, VIIA and VIIB the M*, M, M', M", D, T, Q, x, y, z and w symbols have the same meanings herebefore defined and the D' unit represents the following:

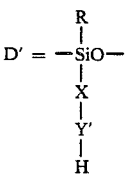

wherein R, Y' and X are as hereinbefore defined.

Illustrative typical Si—H containing silicone starting materials are listed in Table II.

TABLE II

| M | M" | D | D' | T | Q | M" | M' |
|---|---|---|---|---|---|---|---|
| 1 | 0 | 0 | 1.75 | 0 | 0 | 0 | 1 |
| 0 | 0 | 0 | 0 | 0 | 0 | 0 | 0 |
| 1 | 0 | 15 | 5 | 0 | 0 | 0 | 1 |
| 1 | 0 | 10 | 5 | 0 | 0 | 0 | 1 |
| 1 | 0 | 5 | 5 | 0 | 0 | 0 | 1 |
| 0 | 1 | 0 | 4 | 0 | 0 | 1 | 0 |
| 0 | 1 | 4 | 4 | 0 | 0 | 1 | 0 |
| 1 | 0 | 5 | 9 | 0 | 0 | 0 | 1 |
| 1 | 0 | 0 | 10 | 0 | 0 | 0 | 1 |
| 1 | 0 | 10 | 10 | 0 | 0 | 0 | 1 |
| 1 | 0 | 5 | 10 | 0 | 0 | 0 | 1 |

TABLE II-continued

| M | M" | D | D' | T | Q | M'" | M' |
|---|----|---|----|---|---|-----|----|
| 1 | 0 | 5 | 15 | 0 | 0 | 0 | 1 |
| 1 | 0 | 15 | 15 | 1 | 0 | 0 | 2 |
| 1 | 0 | 20 | 20 | 0 | 1 | 0 | 3 |

The ≡Si—H containing compounds represented by Formula (V) are known materials and a specific procedure for preparation is set forth in Example 2 of U.S. Pat. No. 4,046,930 granted Sept. 6, 1977.

The polysiloxanes represented by Formula (I) containing the sterically hindered heterocyclic amine moiety can be used as additives in olefin polymers either as antioxidants and/or heat stabilizers and/or light stabilizers.

In addition to the above-defined compounds of formula (V) it was also found that the tetralkylcyclotetrasiloxanes of the average general formula:

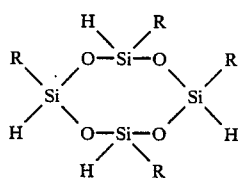

(VIII)

react with the sterically hindered heterocyclic amines to produce the polysiloxanes of the average general formula:

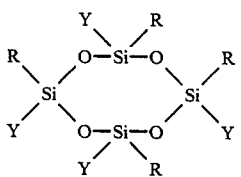

The following examples serve to further illustrate this invention. Parts are by weight unless otherwise specified. In the examples a nitrogen purge was used during the reaction.

EXAMPLE 1

A 50ml 3-neck round bottom flask was fitted with a condenser, thermometer, magnetic stirrer and fittings for introducing a nitrogen atmosphere and was charged with 7.07 g of $MD_y'M_n'$ of the structure:

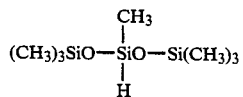

5 g of 2,2,6,6-tetramethyl-4-piperidinol, 10 g of xylene and 5.13 mg of cycloacta-,5-diene diiodoplatinum (II) (35% Pt), eguivalent to 254 ppm Pt based on siloxane. The reaction mixture was heated for four hours at reflux, small amounts of activated charcoal and filter aid were added, the mixture was cooled and filtered to yield a clear brown liguid. This was then vacuum stripped to yield 7.2 g of a clear brown liguid. Yield was about 60% of theory of the polysiloxane containing the sterically hindered 2,2,6,6-tetramethyl-4-piperidinoxy moiety (PIP) having the formula MD*M wherein all of the R groups in the molecules are methyl groups, y has an average value of about 1, and X was nothing. The 2,2,6,6-tetramethyl-4-piperidinoxy moiety herein identified as PIP, has the structure:

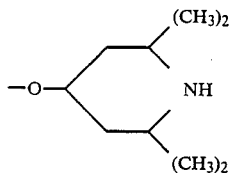

and has replaced the hydogen atom of the

group in the polysiloxane molecule.

EXAMPLE 2

To the reactor described in Example 1 there were added 3,44g of 1,3,5,7-tetramethylcyclotetrasiloxane, 9 g of 2,2,6,6-tetramethyl-4-piperidinol, 10 g of xylene and 2.82 mg of the same platinum catalyst used in Example 1 (287 ppm Pt based on siloxane) and the reaction mixture was stirred and heated. At 89° C. hydrogen evolution was observed. The mixture was heated for 2 hours at 150° C. and then another 3.05 mg of the catalyst was added (596 ppm total Pt) and heated at 150° C. for another hour. The brown liguid was cooled, filtered, stripped on a rotary evaporator and then vacuum stripped. There was recovered 10.5 g of a tacky, viscous brown clear liguid. Yield was about 85% of theory of the polysiloxane, containing the sterically hindered piperidinoxy moiety (PIP), of Formula IX wherein all of the R''' groups are methyl groups, the R' of the Y group is hydrogen and the R group of the Y group are all methyl groups.

EXAMPLE 3

A 200 ml reactor eguipped as described in Example 1 was charged with 44.94 g of $MD_{15}D_5'M'$, 23.55 g of 2,2,6,6-tetramethyl-4-piperidinol, 29.35 g of xylene and 34.02 mg of the same platinum catalyst used in Example 1 (265 ppm Pt based on siloxane) and the mixture was stirred and heated at 100° C. for 5 hours; hydrogen evolution was observed. After standing overnight at room temperature under a nitrogen purge another 270–300 ppm of Pt was added and the reaction mixture was stirred at 140°–142° C. for about 4.5 hours. Small amounts of activated charcoal and filter aid were added, cooled with stirring, stripped on a rotary evaporator at 60° C. at an aspirator vacuum for 1.5 hours, then at 0.1 mm Hg for 1 hour. The residual liguid was pressure filtered to yield a tan turbid liguid that was re-stripped on a vacuum pump for 1 hour at 30°–40° C. and 0.1 mm Hg and filtered to yield about 43.7 g of liquid. Yield was 65.1% of $MD_{15}D_5*M'$, the polysiloxane having the sterically hindered piperidinoxy moiety (PIP), wherein the R' of the Y group is hydrogen and all of the R groups are methyl groups.

EXAMPLE 4

To the reactor described in Example 3 there were added 32.72 g of $MD_{10}D_5'M$, 22.43 g of 2,2,6,6-tetramethyl-4-piperidinol, 23.64 g of xylene and 27.46 mg of the same platinum catalyst used in Example 1 (294 ppm Pt based on siloxane) and the mixture was stirred and heated at 100° C. for 5 hours; hydrogen evolution was observed. After standing overnight at room temperature under a nitrogen purge another 300 ppm Pt was added and the reaction mixture was stirred and heated at 145° C. for about 5.25 hours. Small amounts of activated charcoal and filter aid were added and stirred to cool to room temperature. The reaction mixture was stripped on a rotary evaporator at 55°–60° C. under aspirator vacuum for 2 hours, then at 0.1 mm Hg for 1 hour at 30° C. the residual liguid was pressure filtered to yield 35.1 g of liguid. Yield was 65.3% of $MD_{10}D_5*M'$, the polysiloxane having the sterically hindered piperidinoxy moiety (PIP), wherein the R' of the Y group is hydrogen and all of the R groups are methyl groups.

EXAMPLE 5

A 100 ml reactor eguipped as described in Example 1 was charged with 19.22 g of $MD_5D_5'M'$, 19.03 g of 2,2,6,6-tetramethyl-4-piperidinol, 16.39 g of xylene and 16.45 mg of the same platinum catalyst used in Example 1 (300 ppm Pt based on siloxane) and the mixture was stirred and heated at 100° C. for 5 hours; hydrogen evolution was observed. After standing overnight at room temperature under a nitrogen purge another 300 ppm Pt was added and the reaction mixture was stirred and heated at 140°–143° C. for about 5 hours. Added another 150 ppm Pt, continued the reaction another 1.5 hours; then, while cooling, added small amounts of activated charcoal and filter aid. The reaction mixture was stripped on a rotary evaporator at 60° C. under aspirator vacuum for 1.25 hours. The residual liguid was pressure filtered to yield 23.7 g of clear tan liguid. Yield was 63.8% of $MD_5D_5*M'$, the polysiloxane, having the sterically hindered piperidinoxy moiety (PIP), wherein the R' of the Y group is hydrogen and all of the R groups are methyl groups.

EXAMPLE 6

To the reactor described in Example 5 there were added 26.84 g of $MD_y'M'$, 19.92 g of 2,2,6,6-tetramethyl-4-piperidinol, 20.04 g of xylene and 20.44 mg of the same platinum catalyst used in Example 1 (267 ppm Pt based on siloxane) and the mixture was stirred and heated. At about 80–85° C. the mixture was brown with gas evolution observed. At 140° C. the mixture went to a black brown color and heating was continued at 138°–140° C. for 3.5 hours. Cooled to room temperature, added small amounts of activated charcoal and filter aid and filtered to obtain a clear light tan liguid. Stripped at aspirated vacuum on a rotary evaporator to 45°–50° C. and then to 1 mm Hg at 45°–50° C. The product became white opaque was filtered to yield a clear light tan liguid. Upon standing a solid phase separated out, the mixture was filtered and then distilled at 101° C. at 1 mm Hg to yield 28.3 g of water white liguid. Yield was 62.1% of $MD_y*M'$, the polysiloxane, having the sterically hindered piperidinoxy moiety (PIP), wherein the R' of the Y group is hydrogen and all of the R groups are methyl groups, and y has an average value of about 1.

EXAMPLE 7

A 250 ml reactor eguipped as described in Example 1 was charged with 41.84 g of $M''D_4'M''$ of the formula:

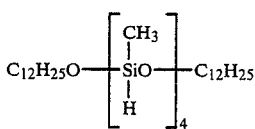

37.01 g of 2,2,6,6-teramethyl-4-piperidinol, 33.79 g of xylene and 35.9 mg of the same platinum catalyst used in Example 1 (300 ppm Pt based on siloxane) and the mixture was heated at reflux for 1.5 to 2 hours; hydrogen evolution was observed. Added another 336 ppm Pt, continued the reaction 1 hour at 140° C. and let stand overnight at room temperature under nitrogen. Small amounts of activated charcoal and filter aid were added and filtered to obtain a clear tan liquid. Stripped at aspirated vacuum in a rotary evaporator at 50° C., then at 50° C. and 1 mm Hg to yield a turbid liguid that was pressure filtered to give 54.1 g of clear tan liguid. Yield was 70.6% of the sterically polysiloxane, having the hindered piperidinoxy moiety (PIP), of the general formula $M''D_4*M''$.

EXAMPLE 8

To the reactor described in example 7 there were added 57.99 g of $M''D_4D_4'M''$ of the formula:

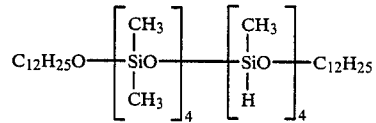

0.14 g of 2,2,6,6 tetramethyl-4-piperidinol, 42.06 g of xylene and 51.5 mg of the same catalyst used in Example 1 (311 ppm Pt based on siloxane). At about 40° C. hydrogen evolution was observed, stirred at reflux for 4.5 hours and cooled overnight under nitrogen. Small amounts of activated charcoal and filter aid were added and pressure filtered. Stripped at aspirated vacuum on a rotary evaporator at 45°–50° C. and then at 50° C. at 1 mm Hg. The tan liguid was filtered to yield 75.84 g of the polysiloxane, having the sterically hindered piperidinoxy moiety (PIP), of the general formula $M''D_4D_4*M''$; yield was 79.2%.

EXAMPLE 9

In a manner similar to that described in Example 5 a mixture of 66.98 g of $MD_5M_5'M'$ of the formula:

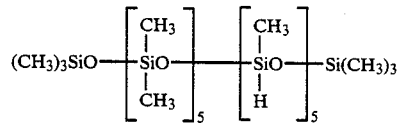

68.19 g of 1,2,6,6-tetramethyl-4-piperidinol, 57.93 g of xylene and 57.9 mg of the same platinum catalyst (303 ppm Pt based on siloxane) was refluxed for 1.5 hours. Then an additional 150 ppm Pt was added and continued refluxing for 2 hours. Added small amounts of activated charcoal and filter air, cooled and pressure filtered. The tan liguid was desolvated on the rotary evaporator to 50° C. at aspirated vacuum then at pump vacuum to 45°–50° C. at 1 mm Hg and refiltered to give 84.5 g of clear tan liguid. Yield was 64% of the polysiloxane, having the sterically hindered piperidinoxy moiety (PIP), of the general formula MD$_5$D$_5$*M',

EXAMPLE 10

In a manner similar to that described in Example 4 a mixture of 71.83 g of MD$_{10}$D$_5$'M' of the general formula:

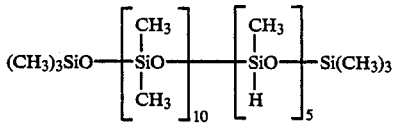

50.04 g of 2,2,6,6-tetramethyl-4-piperidinol, 52.23 g of xylene and 61.81 mg of the same platinum catalyst (301 ppm Pt based on siloxane) was refluxed for about 3 hours and then left standing overnight under nitrogen. After adding an additional 100 ppm Pt and refluxing for about 2 hours, small amounts of activated charcoal and filter aid were added and the mixture was cooled and pressure filtered. The tan liquid was desolvated at 50° C. on the rotary evaporator at aspirated vacuum then at pump vacuum at 50° C. at 1 mm Hg and filtered to give 80.1 g of clear, slightly tan liquid. Yield was 67% of the polysiloxane, having the sterically hindered piperidinoxy moiety (PIP), of the general formula MD$_{10}$D$_5$*M'.

EXAMPLE 11

In a manner similar to that described in Example 3 a mixture of 100.63 g of MD$_{15}$D$_5$'M of the general formula:

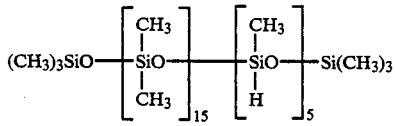

52.74 g of 2,2,6,6-tetramethyl-4-piperidinol, 65.73 g of xylene and 88.93 mg of the same platinum catalyst (309 ppm Pt based on siloxane) was refluxed for 4.5 hours and then left standing overnight under nitrogen. After adding an additional 100 ppm Pt and refluxing for 2 hours, activated charcoal and filter and were added and the mixture was cooled and pressure filtered. The tan liquid was desolvated on the rotary evaporator at aspirated vacuum at 50° C. then at pump vacuum at 45°–50° C. at 1 mm Hg and filtered to give 108.6 g of clear, very slightly tan liquid. Yield was 72% of the polysiloxane, having the sterically hindered piperidinoxy moiety of the general formula MD$_{15}$D$_5$*M'.

EXAMPLE 12

In a manner similar to that described in Example 7 a mixture of 63.26 g of M"D$_4$'M", 55.96 g of 2,2,6,6-tetramethyl-4-piperidinol, 51.1 g of xylene and 54.88 mg of the same platinum catalyst (303.6 ppm Pt based on siloxane) was refluxed for about 4.5 hours and then left standing overnight under nitrogen. In the morning added 1.33 g of 2,2,6,6-tetramethyl-4-piperidinol and refluxed for 2 hours. Added activated charcoal and filter aid, cooled and pressure filtered. The tan liquid was desolvated on the rotary evaporator at aspirated vacuum at 50° C. then at pump vacuum at 50° C. at 1 mm Hg. The mixture was pressure filtered to give 84.7 g of clear, slightly tan liquid. Yield was 72.7% of the polysiloxanes, having the sterically hindered piperidinoxy moiety (PIP), of the general formula M"D$_4$*M".

EXAMPLE 13

In a manner similar to that described in Example 8, 78.53 g of M"D$_4$D$_4$'M", 54.36 g of 2,2,6,6-tetramethyl-4-piperidinol, 56.75 g of xylene and 67.64 mg of the same platinum catalyst (301 ppm Pt based on siloxane) was refluxed for about 4–5 hours and then left standing overnight under nitrogen. Added another 150 ppm Pt, refluxed for 2.5 hours, added activated charcoal and filter aid, cooled and pressure filtered. The dark tan clear liquid was desolvated on the rotary evaporator at aspirated vacuum at 50° C. and then at pump vacuum at 50° C. at 1 mm Hg for 2 hours. The mixture was filtered to give 99.7 g of clear tan liquid. Yield was 76.5% of the polysiloxane having the sterically hindered piperidinoxy moiety (PIP), of the general formula M"D$_4$D$_4$*M".

EXAMPLE 14

To the reactor similar to that described in Example 1 there were charged 63.6 g of toluene, 19.3 g of 2,2,6,6-tetramethyl-4-piperidinol and two potassium hydroxide pellets and the mixture was refluxed to azeotropically remove any water present. Over a 15 minutes period at a temperature of 80°–90° C. 18.58 g of MD$_5$D$_9$'M' of the formula:

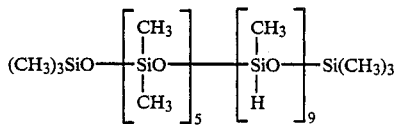

was added in a dropwise manner and the mixture was stirred an additional hour. The mixture was cooled and neutralized, first with sodium acetate and followed by potassium carbonate, and stirred overnight. The toluene was stripped under vacuum to 110° C. pot temperature and the liquid residue was pressure filtered hot to give 26 g of colorless product. Yield was 70% of the polysiloxane, having the sterically hindered piperidinoxy moiety (PIP), of the general formula MD$_5$D$_9$*M'.

EXAMPLE 15

To the reactor similar to that described in Examples 5 there were charged 157.25 g of 2,2,6,6-tetramethyl-4-piperidinal and 15.87 g of xylene and azeotropically distilled at about 165° C. to remove water present. Cooled to 104° C. and slowly (15 minutes) added 76.3 g of MD'$_{10}$M' of the formula:

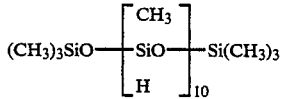

after having added 8 ml of xylene and 10.58 mg of the same platinum catalyst (100 ppm Pt based on siloxane). The temperature was gradually raised to 130° C. and the reaction was continued overnight at 128° C. Added activated charcoal and filter and, cooled pressure filtered. The filtrate was desolvated on the rotar evaporator at 80° C. at aspirated vacuum and then at pump vacuum at 100° C. at 1 mm. Hg. The mixture was filtered and 26.4 g of light tan liquid was precovered. Yield was 76.4% of the polysiloxane, having the sterically hindered piperidinoxy moiety (PIP), of the general formula $MD^*_{10}M'$.

EXAMPLE 16

Following the procedure similar to that of Example 15, 113.45 g of $MD_5D'_{10}M$ of the structure

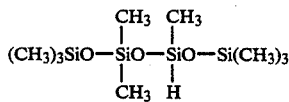

and 157.25 g of 2,2,6,6-tetramethyl-4-piperidinol were reacted in about 18 g of xylene using 12.21 mg of the same platinum catalyst (100 ppm based on siloxane). After stirring overnight at 140° C. the product was recovered as a light brown liguid, 29.8 g. Yield was 73.8% of the polysiloxane, having the sterically hindered piperidinoxy moiety (PIP), of the general formula $MD_5D^*_{10}M'$.

EXAMPLE 17

Following the procedure similar to that of Example 15, 95.67 of $MD_5D'_{15}M'$ of the structure:

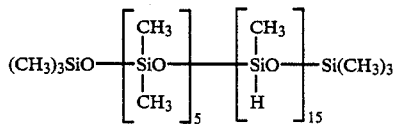

and 157.25 g of 2,2,6,6-tetramethyl-4-poperidinol were reacted with about 18 g of xylene using 11.85 mg of the same platinum catalyst (100 ppm Pt based on siloxane). After stirring overnight at 128° C. the product was recovered as a light brown liguid, 31.5 g. Yield was 80.7% of the polysiloxane, having the sterically hindered piperidinoxy moiety (PIP), of the general formula $MC_5D^*_{15}M'$.

EXAMPLE 18

Using a 250 ml reactor and following the procedure similar to that of example 15, 150.53 g of $MD_{10}D'_{10}M'$ of the structure:

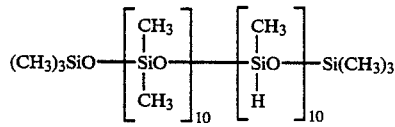

and 157.25 g of 2,2,6,6-tetramethyl-4-poperidinol were reacted with about 20.3 g of xylene using 13.56 mg of the same platinum catalyst (100 ppm based on siloxane). After stirring overnight at 130°–135° C. the product was recovered as a light gold liguid, 31 g. Yield was 67% of the polysiloxane, having the sterically hindered piperidinoxy moiety (PIP), of the general formula $MC_{10}D^*_{10}M'$.

Several sterically hindred piperidinoxy polysiloxanes prepared as described in the examples were evaluated as UV stabilizers in olefin polymers. The test samples were prepared by initially preparing separate masterbatches of each stabilizer composition with a virgin ethylene-1-butene copolymer produced by the catalytic process disclosed in U.S. Pat. No. 4,508,842 (Polyolefin A). Each masterbatch contained the selected polyslioxane stabilizer composition at a concentration of 5 weight percent Portions of each masterbatch were used to prepare the olefin polymer compositions for evaluation; this procedure provided for more accurate addition of the desired amount of stabilizer composition to the olefin polymer. An accurately weighed amount (10 g) of the stabilizer composition was added to a weighed amount (2,270 g) of the olefin polymer to provide a total concentration of 1,000 ppm of the stabilizer in the blend. Each mixture was mixed for five minutes to ensure thorough mixing and dispersion and then extruded using a Brabender Plasticorder ® ) extruder fitted with a one inch diameter extruder screw, a 25:1 length/diameter ratio and a 2 inch by 0.125 inch tape die. All zones of the extruder, including the die, were heated to 180° C. prior to the performance of the balance of the procedure.

The extruder was purged for 10 minutes at 50 rpm with an additional guantity of the virgin, non-stabilized olefin polymer and this was followed by introduction of the stabilized olefin polymer composition prepared above. The stabilized olefin polymer composition was extruded for a period of 5 minutes and collected as a 0.125 inch thick tape. The extruder was then purged with an additional guantity of the virgin, non-stabilized olefin polymer followed by the subseguent batch of stabilized copolymer compoistion. This alternating procedure was repeated for the preparation of the tapes for each stabilized olefin polymer composition.

The tape extrudates were pressed at 165° C. to form 6 inch by 6 inch by 0.025 inch thick plaques and each plaque was cut in half to form 3 inch by 6 inch by 0.025 inch thick samples that would fit into the holder on the Weatherometer. Eight such samples for each stabilized olefin polymer composition were prepared and they were exposed to repeating cycles of 8 hours exposure to UV light at 60° C. and 4 hours exposure to condensation at 40° C. using the procedure described in ASTM D 4329-84. The percent elongation was measured after various periods of exposure and from these values the 50 percent retained elongation was calculated.

For comparative purposes the same olefin polymer was tested without additives and with conventional, heretofore available additives.

The results on the stability of Polyolefin A are shown in Table III; the materials used were:

Polyolefin A—the ethylene-1-butene copolymer of U.S. Pat. No. 4,508,842 described supra.
PS—A—a polysiloxane of Example 9 structure.
PS—B—a polysiloxane of Example 10 structure.
PS—C—a polysiloxane of Example 11 structure.
PS—D—a polysiloxane of Example 12 structure.
PS—E—a polysiloxane of Example 13 structure.
PS—F—a polysiloxane of Example 15 structure.
PS—G—a polysiloxane of Example 16 structure.
PS—H—a polysiloxane of Example 17 structure.
PS—I—a polysiloxane of Example 18 structure.
Additive 1—octadecyl 3-(3,5 di-tert- butyl-4-hydroxyphenyl)propionate.
Additive 2—zinc stearate.
Additive 3—tris (2,4-di-tert-butylphenyl) phosphite.
Additive 4—N,N-2-hydroxyethylstearyl amine

TABLE III

| Run | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| PS-A | 1000 | | | | | | 1000 | | | | | | | |
| PS-B | | 1000 | | | | | | | | | | | | |
| PS-C | | | 1000 | | | | | | | | | | | |
| PS-D | | | | 1000 | | | | | | | | | | |
| PS-E | | | | | 1000 | | | | | | | | | |
| PS-F | | | | | | 1000 | | | | | | | | |
| PS-G | | | | | | | | | 1000 | | | | | |
| PS-H | | | | | | | | | | 1000 | | | | |
| PS-I | | | | | | | | | | | 1000 | | | |
| Add. 1 | | | | | | | | | | | | 300 | 300 | 300 |
| Add. 2 | | | | | | | | | | | | 500 | 500 | 500 |
| Add. 3 | | | | | | | | | | | | | 600 | |
| Add. 4 | | | | | | | | | | | | 500 | 500 | 500 |
| Hours UV Exp. to 50% Retained Elongation | 350 | 280 | 235 | 225 | 175 | 390 | 325 | 385 | 430 | 290 | 35 | 35 | 35 | 35 |

Add. = Additive
Amounts of polysiloxane and additive are given in ppm.

Runs 1 to 10 contained 1,000 ppm of the polysiloxanes of this invention blended with Polyolefin A. Table III reports the hours of UV exposure to 50% Retained Elongation.

What we claim is:

1. A polysiloxane of the formula:

$$M^*_v D_x D^*_y T_z Q_w M^*_v \quad (I)$$

wherein:

M* represents a member of the group M, M' or M" in which
$M = R^u{}_3 SiO-$;
$M' = R^u{}_3 Si-$;
$M'' = R''O_{\frac{1}{2}}-$;

$R^u$ is an alkyl group having from 1 to about 8 carbon atoms, phenyl or phenethyl;

R" is an alkyl group having from 2 to about 40 carbon atoms or a phenyl group;

$$D = \begin{array}{c} R \\ | \\ -SiO- \\ | \\ R \end{array};$$

R is phenyl or an alkyl group having from 1 to 3 carbon atoms;

$$D^* = \begin{array}{c} R^u \\ | \\ -SiO- \\ | \\ X \\ | \\ Y' \\ | \\ (CH_2)_p \diagdown Z \\ R \diagup \diagdown R' \\ R \quad N \quad R \\ | \\ R'''' \end{array}$$

R' is hydrogen, an alkyl group having from 1 to 3 carbon atoms or a keto oxygen;

X is a valence bond or a divalent linkage selected from the group consisting of $-C_nH_{2n}-$, $-C_nH_{2n}OC_mH_{2m}-$,

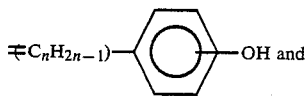

$-C_nH_{2n}O(C_mH_{2m-1}\mp OH$;

R'''' is hydrogen or an alkyl group having from 1 to about 12 carbon atoms;

Y' is $-O-$, $-COO-$, $-C_nH_{2n}O-$ or $-NH-$;

Z is carbon or nitrogen, with the proviso that when z is nitrogen Y' is $-C_nH_{2n}O-$ n has a value of from zero to about 10;
m has a value of from zero to about 10;
p has a value of zero or one;

$$T = \begin{array}{c} R \\ | \\ SiO_{3/2}- \\ | \end{array};$$

$$Q = \begin{array}{c} | \\ SiO_{4/2}- \\ | \end{array};$$

v has a value of 1;
x has a value of from zero to about 200;
y has a value of from 1 to about 100;
z has a value of from zero to about 5;
w has a value of from zero to about 5.

2. A polysiloxane as claimed in claim 1 of the formula:

$$MD_x D^*_y T_z Q_w M' \quad (IIA)$$

wherein M, D, D*, T, Q, M', x, y, z and w are as defined in claim 1.

3. A poysiloxane as claimed in claim 1 of the formula:

$$M''D_x D^*_y T_z Q_w M'' \quad (IIB)$$

wherein M", D, D*, T, Q, x, y, z and w are as defined in claim 1.

4. A polysiloxane as claimed in claim 1 of the formula:

$$MD_x D^*_y M' \quad (IIIA)$$

wherein M, D, D*, M', x and y are as defined in claim 1.

5. A polysiloxane as claimed in claim 1 of the formula:

M''D_xD_y*M''  (IIIB)

wherein M'', D, D*, x and y are as defined in claim 1.

6. A polysiloxane as claimed in claim 1 wherein all of the R groups are methyl.

7. A polysiloxane as claimed in claim 2 wherein all of the R groups are methyl.

8. A polysiloxane as claimed in claim 3 wherein all of the R groups are methyl.

9. A polysiloxane as claimed in claim 4 wherein all of the R groups are methyl.

10. A polysiloxane as claimed in claim 5 wherein all of the R groups are methyl.

11. A polysiloxane as claimed in claim 4 wherein x is zero.

12. A polysiloxane as claimed in claim 5 wherein x is zero.

13. A polysiloxane as claimed in claim 1 wherein $R^u$ is an alkyl group having from 1 to 3 carbon atoms; R'' is an alkyl group having from about 12 to about 18 carbon atoms; R' is hydrogen; X is nothing; R'''' is hydrogen; Y' is —O—; Z is carbon; p has a value of 1; v has a value of 1; x has a value of from 1 to about 20; y has a value of from 1 to 20; and z and w are zero.

14. A polysiloxane as claimed in claim 13 wherein X is $-C_nH_{2n}-$.

15. A polysiloxane as claimed in claim 4 wherein x and y each have a value of from 1 to about 20.

16. A polysiloxane as claimed in claim 5 wherein x and y each have a value of from 1 to about 20.

17. A polysiloxane as claimed in claim 15 wherein all of the R groups are methyl.

18. A polysiloxane as claimed in claim 16 wherein all of the R groups are methyl.

19. A polysiloxane as claimed in claim 4 of the structure:

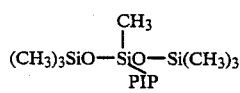

wherein PIP is:

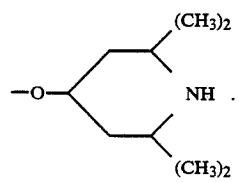

20. A polysiloxane as claimed in claim 4 of the structure:

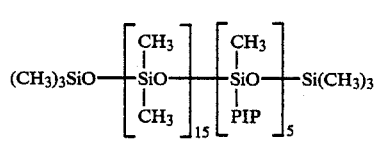

wherein PIP is

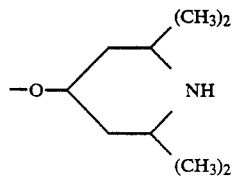

21. A polysiloxane as claimed in claim 4 of the structure:

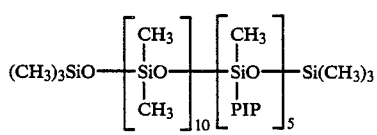

wherein PIP is

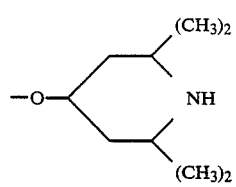

22. A polysiloxane as claimed in claim 4 of the structure:

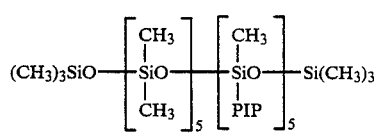

wherein PIP is

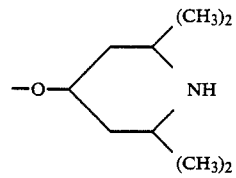

23. A polysiloxane as claimed in claim 4 of the structure:

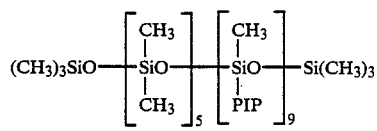

wherein PIP is

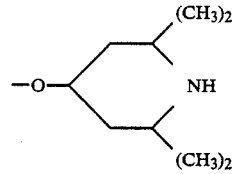

24. A polysiloxane as claimed in claim 4 of the structure:

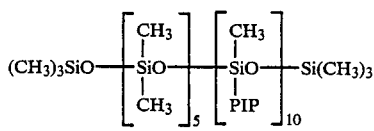

wherein PIP is

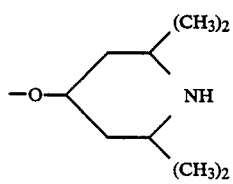

25. A polysiloxane as claimed in claim 4 of the structure:

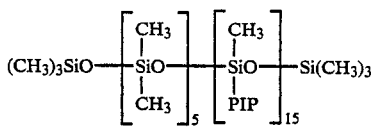

wherein PIP is

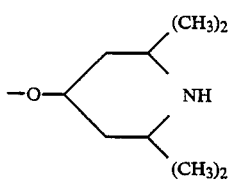

26. A polysiloxane as claimed in claim 4 of the structure:

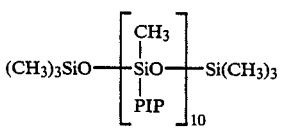

wherein PIP is

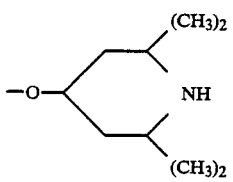

27. A polysiloxane as claimed in claim 4 of the structure:

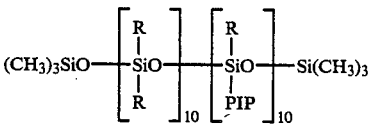

wherein PIP is

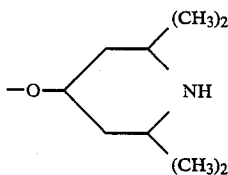

28. A polysiloxane as claimed in claim 5 of the structure:

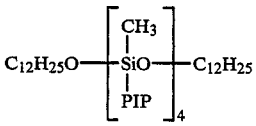

wherein PIP is

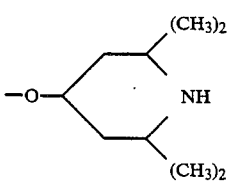

29. A polysiloxane as claimed in claim 5 of the structure:

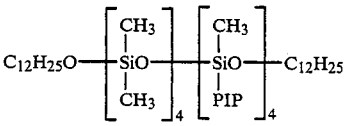

wherein PIP is

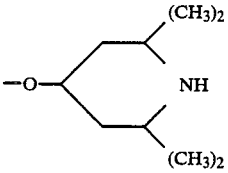

30. A polysiloxane of the structure:

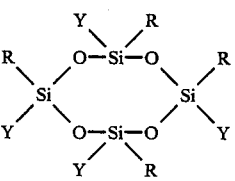

wherein Y is the group:

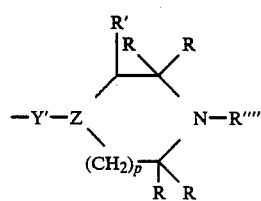
wherein Y', Z, R, R', R'''' and p are as defined in claim 1.
31. A polysiloxane as claimed in claim 30 wherein R is methyl and Y is PIP as defined
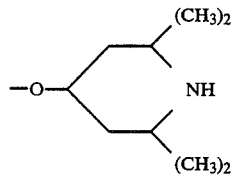
* * * * *